United States Patent
Chu (10) Patent No.: US 9,945,788 B2
(45) Date of Patent: Apr. 17, 2018

(54) METHODS AND SYSTEMS FOR DETERMINING OPTICAL REGIONS OF INTEREST

(71) Applicant: LIFE TECHNOLOGIES CORPORATION, Carlsbad, CA (US)

(72) Inventor: Yong Chu, Castro Valley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/016,564

(22) Filed: Feb. 5, 2016

(65) Prior Publication Data

US 2016/0231250 A1 Aug. 11, 2016

Related U.S. Application Data

(60) Provisional application No. 62/113,058, filed on Feb. 6, 2015.

(51) Int. Cl.
*G01N 21/76* (2006.01)
*G01N 21/27* (2006.01)
(Continued)

(52) U.S. Cl.
CPC ......... *G01N 21/763* (2013.01); *G01N 21/274* (2013.01); *G01N 21/6452* (2013.01);
(Continued)

(58) Field of Classification Search
None
See application file for complete search history.

(56) References Cited

U.S. PATENT DOCUMENTS 6,518,068 B1 * 2/2003 Gambini ............... G01N 21/15
250/361 C
7,630,849 B2 * 12/2009 DeSimas ............... G01N 31/00
600/1
(Continued)

FOREIGN PATENT DOCUMENTS

WO 2013049776 A1 4/2013
WO 2014153369 A1 9/2014

OTHER PUBLICATIONS

Ho, Jinn, et al., Gridding Spot Centers of Smoothly Distorted Microarray Images, IEEE Transactions on Image Processing, Feb. 2006, pp. 342-353, vol. 15—No. 2.
(Continued)

*Primary Examiner* — Edwin Gunberg
(74) *Attorney, Agent, or Firm* — Mauriel Kapouytian Woods LLP; Elaine Lee; Michael Mauriel (57) ABSTRACT

The present teachings relate to a method and system for determining Regions of Interest (ROI) for one or more biological samples in a laboratory instrument. The method can include an optical system capable of imaging florescence emission from a plurality of sample wells. An initial ROI, its center location and size can be estimated from the fluorescence detected from each well. From this information the average size of the ROIs can be determined and global gridding models can be derived to better locate each of the ROIs. The global gridding models can then be applied to the ROIs to improve the precision of the ROI center locations. Sample wells not originally providing fluorescence ROIs can be recovered through the use of mapping functions. The radius of each ROI can then be adjusted to improve the signal-to-noise ratio of the optical system.

20 Claims, 8 Drawing Sheets

(51) Int. Cl.
    *G01N 21/77*     (2006.01)
    *G06K 9/00*     (2006.01)
    *G06K 9/32*     (2006.01)
    *G01N 21/64*     (2006.01)

(52) U.S. Cl.
    CPC ........... *G01N 21/77* (2013.01); *G06K 9/0014* (2013.01); *G06K 9/00134* (2013.01); *G06K 9/3233* (2013.01); *G01N 21/6428* (2013.01); *G01N 21/6456* (2013.01); *G01N 2021/7786* (2013.01); *G01N 2201/127* (2013.01)

(56) References Cited

U.S. PATENT DOCUMENTS

| | | |
|---|---|---|
| 7,817,273 B2 | 10/2010 | Bahatt et al. |
| 2004/0234114 A1 | 11/2004 | Amakawa et al. |
| 2007/0100569 A1* | 5/2007 | DeSimas ................ G01N 31/00 702/85 |
| 2012/0015825 A1 | 1/2012 | Zhong et al. |

OTHER PUBLICATIONS

Biosearch Technologies, CAL FLOUR and QUASAR DYES Thermal Cycler Spectral Calibration Instructions, 2014, pp. 1-22, Biosearch Technologies, Inc.

* cited by examiner

METHODS AND SYSTEMS FOR DETERMINING OPTICAL REGIONS OF INTEREST

CROSS-REFERENCE TO RELATED APPLICATIONS

This application claims the benefit of priority of U.S. provisional application Ser. No. 62/113,058, filed Feb. 6, 2015, which is incorporated herein by reference in its entirety.

BACKGROUND

Installation and calibration of laboratory instrumentation can be a time consuming and expensive process. In many cases, engineers from the instrument supplier must be on site to perform these processes. This cost is generally passed on to the user. In some cases, experienced users can successfully calibrate properly manufactured instruments using multi-step procedures. During such calibrations, physical standards and well plates may be used in combination with manual procedures. Manual calibration processing and data inspection is error prone and may rely on ad hoc or subjective measures. While a final system verification step may provide resilience against accepting suboptimal calibrations, automation offers improved objectivity and uniformity during such activities. The present teachings can incorporate expert knowledge into an automated calibration and verification system providing pass/fail status and troubleshooting feedback when a failure is identified. If an instrument should fail the calibration process, then a service engineer can be called. The present teachings can minimize the cost of, and time required for, the installation and calibration procedures.

SUMMARY OF THE INVENTION

The present teachings relate to a method and system for determining a Region of Interest (ROI) for one or more biological samples in a laboratory instrument. In an embodiment of the present invention, the method comprises an optical system capable of imaging florescence emission from a plurality of sample wells. An initial ROI, its center location and size can be estimated from the fluorescence detected from each well. From this information the average size of the ROIs can be determined and global gridding models can be derived to better locate each of the ROIs. The global gridding models can then be applied to the ROIs to improve the precision of the ROI center locations. Sample wells not originally providing fluorescence ROIs can be recovered through the use of mapping functions. The radius of each ROI can then be adjusted to improve the signal-to-noise ratio of the optical system.

In another embodiment, each sample well contains a biological sample.

In another embodiment, each biological sample is excited by a light source.

In another embodiment, the biological sample fluoresces at a predetermined wavelength in response to the excitation.

In another embodiment, the fluorescence is detected by the optical system.

In another embodiment, the biological samples comprise spectrally distinguishable dyes.

In another embodiment, the global gridding models comprise comparing the center-to-center distance between ROIs to grid co-ordinates of a well plate layout to determine an X and Y grid co-ordinate for each ROI.

In another embodiment, mapping functions are determined and applied to the X and Y co-ordinates for each ROI to map each co-ordinate to the center of each ROI.

According to various embodiments a system for calibrating region of interest (ROI) locations is presented. The system can comprise a computer system comprising at least one processor and at least one computer-readable medium. The system can further comprise at least one input device, at least one display and an optical detection system. The optical detection system can further comprise a plurality of filters, at least one excitation source, at least one detector and a microwell tray.

In various embodiments the at least one computer-readable medium is coupled to at least one processor and comprises instructions executable by the processor.

In various embodiments the instructions executable by the processor comprise at least one step for determining ROIs and automates the calibration of the ROIs.

In various embodiments the plurality of filters comprises at least one excitation filter, at least one emission filter and at least one beam splitter.

In various embodiments the microwell tray contains at least one biological sample comprising at least one fluorescent dye.

In other embodiments the at least one display provides information to a user.

In other embodiments the at least one input device comprises alphanumeric and other keys configured to communicate information to the processor and cursor control to communicate direction information to the processor.

DESCRIPTION

The following description of various embodiments is merely exemplary in nature and is in no way intended to limit the present teachings, applications or uses. Although the present teachings will be discussed in some embodiments as relating to polynucleotide amplification, such as polymerase chain reaction (PCR), such discussion should not be regarded as limiting the present teaching to only those applications.

Figure 1:
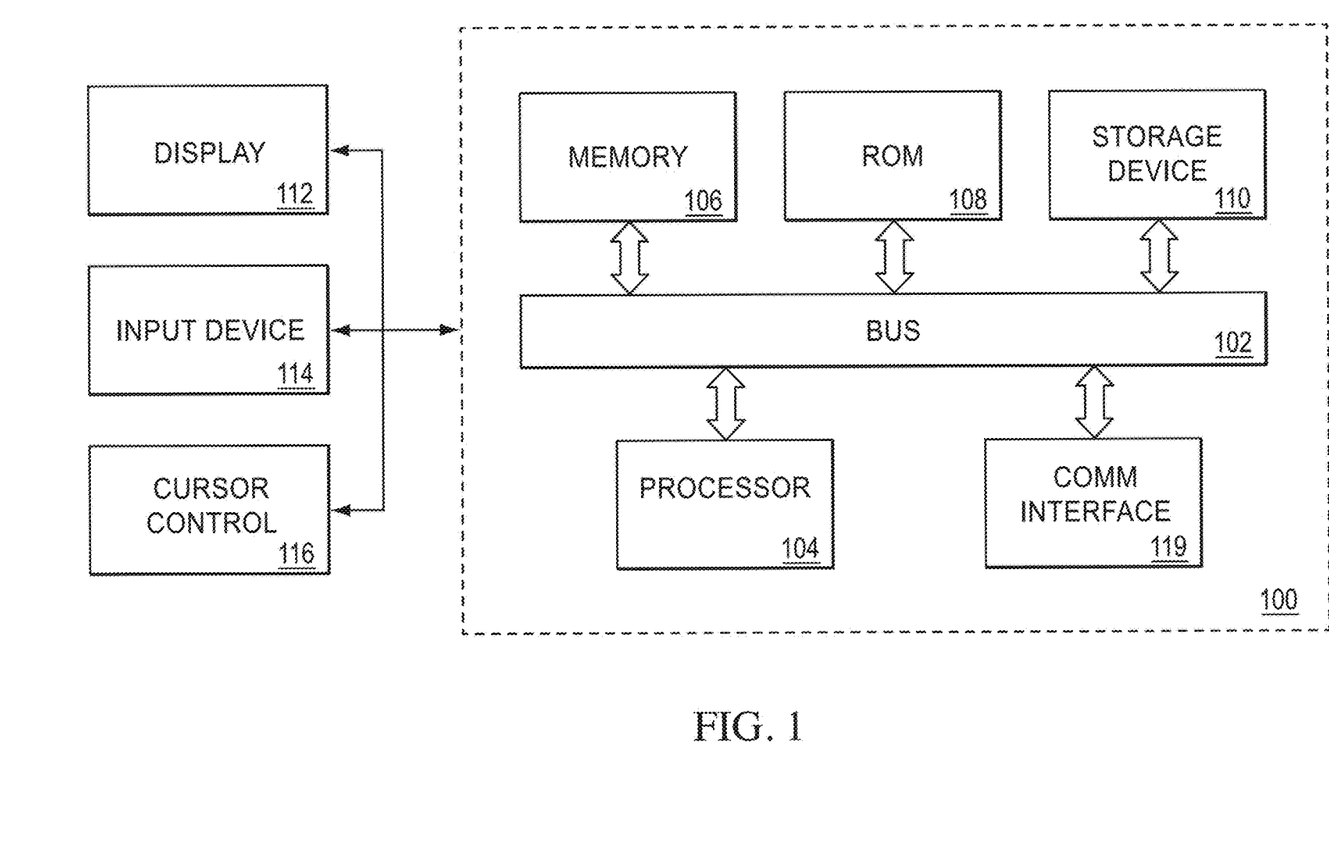
FIG. 1 illustrates a computer system on which embodiments of the present teachings can be implemented.

FIG. 1 is a block diagram that illustrates a computer system 100 upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM), or other dynamic storage device, coupled to bus 102, and instructions to be executed by processor 104. Memory 106 also may be used for storing temporary variables or other intermediate information during execution of instructions, corresponding to the methods and present teachings, to be executed by processor 104. Computer system 100 further includes a read only memory (ROM) 108 or other static storage device coupled to bus 102 for storing static information and instructions for processor 104. A storage device 110, such as, for example, but not limited to a solid-state disk, a magnetic disk or optical disk is provided and coupled to bus 102 for storing information and instructions.

Computer system 100 may be coupled via bus 102 to a display 112, such as, for example, but not limited to a cathode ray tube (CRT) or liquid crystal display (LCD), for displaying information to a computer user. A user input device 114, including alphanumeric and other keys, is coupled to bus 102 for communicating information and command selections to processor 104. Another type of user input device is cursor control 116, such as, for example, but not limited to a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

Consistent with certain embodiments of the present teachings, setup and calibration of laboratory instruments can be performed by computer system 100 in response to processor 104 executing one or more sequences of one or more instructions contained in memory 106. Such instructions may be read into memory 106 from another computer-readable medium, such as, for example storage device 110. Execution of the sequences of instructions contained in memory 106 causes processor 104 to perform the process states described herein. Alternatively hard-wired circuitry may be used in place of, or in combination with, software instructions to implement the present teachings. Thus, implementations of the present teachings are not limited to any specific combination of hardware circuitry and software.

The term "computer-readable medium" as used herein refers to any media that participates in providing instructions to processor 104 for execution. Such a medium may take many forms, including but not be limited to, nonvolatile media, volatile media, and transmission media. Nonvolatile media can include but not be limited to, for example, optical or magnetic disks, such as storage device 110. Volatile media can include, but not be limited to dynamic memory, such as memory 106. Transmission media can include, but not be limited to coaxial cables, copper wire, and fiber optics, including the wires that comprise bus 102. Transmission media can also take the form of acoustic or light waves, such as those generated during radio-wave and infrared data communications.

Common forms of computer-readable media can include, for example, but not be limited to a floppy disk, flexible disk, hard disk, magnetic tape, or any other magnetic medium, a CDROM, any other optical medium, punch cards, paper tape, any other physical medium with patterns of holes, a RAM, PROM, EPROM, FLASH-EPROM, USB drive, jump drive or any other memory chip or cartridge, a carrier wave, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over, for example, a telephone line using a modem or wireless network. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

The present teachings are described with reference to Real-Time Polymerase Chain Reaction (RT-PCR) instruments. In particular, an embodiment of the present teachings is implemented for RT-PCR instruments employing optical imaging of well plates. Such instruments can be capable of simultaneously or sequentially measuring signals from a plurality of samples or spots for analytical purposes and often require calibration, including but not limited to processes involving: identifying ROI (Regions of Interest), determining background signal, uniformity and pure dye spectral calibration for multicomponent analysis. Calibration may also involve a RT-PCR verification reaction using a known sample plate with an expected outcome. One skilled in the art will appreciate that while the present teachings have been described with examples pertaining to RT-PCR instruments, their principles are widely applicable to other forms of laboratory instrumentation that may require calibration and verification in order to ensure accuracy and/or optimality of results.

The present teachings can be applied to RT-PCR instrument systems. Such RT-PCR instruments are well known to one skilled in the art. For example the present teachings can be applied to instruments such as, for example, but not limited to the Applied Biosystems Sequence Detection Systems 7500/7900/ViiA7 and Quant Studio systems, the Roche Applied Science LightCycler® 2.0 PCR amplification and detection system, the Bio-Rad MyiQ Single-Color Real-Time PCR Detection System, or the Stratagene Mx3000P™ Real-Time PCR System. Such instruments generally use some form of imaging system. While the present teachings are discussed relative to a CCD (charge coupled detector) imaging system, the present teachings can be easily adapted to any form of imaging system.

In a system with a CCD imaging system, a CCD camera images a sample plate (typically a 96-well plate, although plates with other numbers of wells can be used or sample blocks containing individual tubes can also be used) at various selected dye fluorescent emission wavelengths during a PCR run. In such instruments, the wells are generally illuminated by an excitation light at wavelengths appropriate to each dye. In order to use the RT-PCR system to accurately monitor PCR amplification using the well emission intensities, the system must be calibrated for each dye emission.

Figure 2:
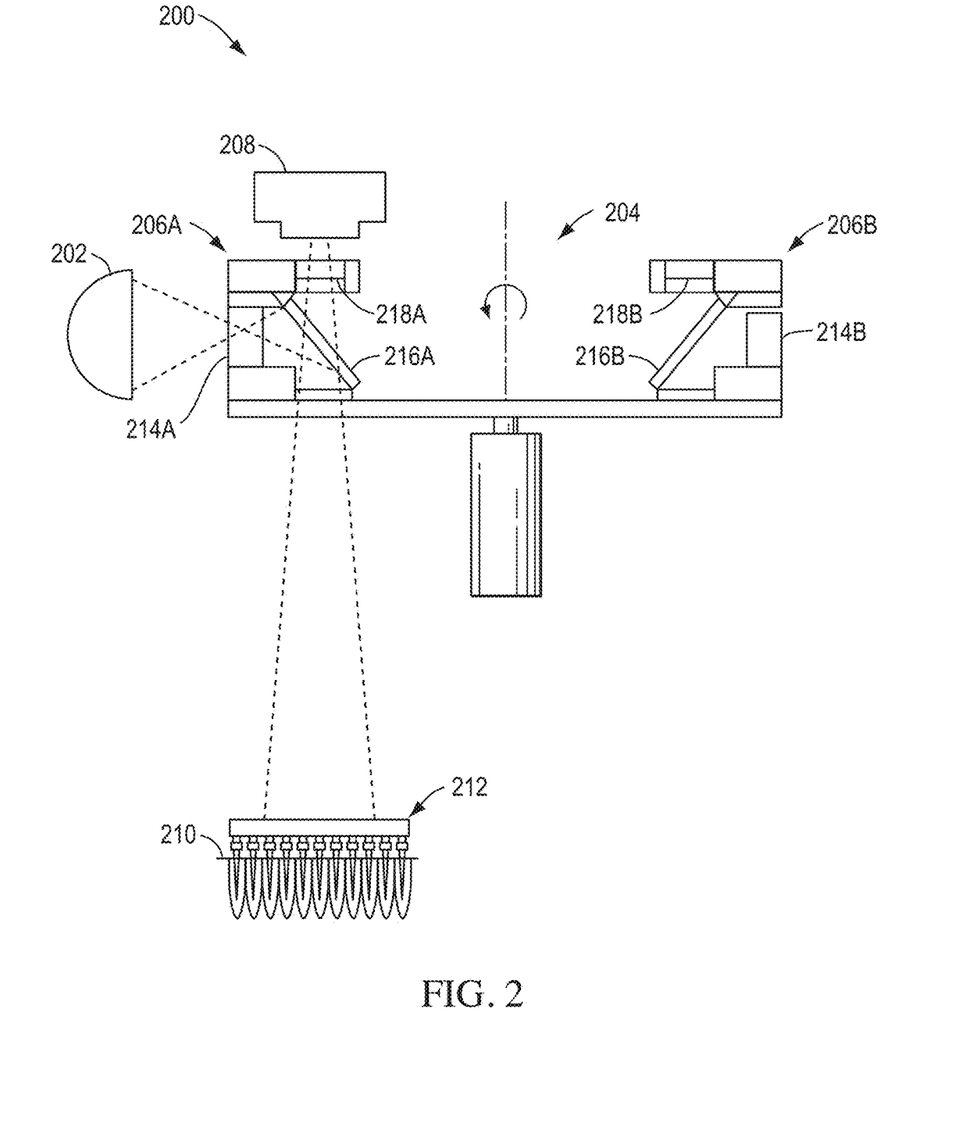
FIG. 2 illustrates a laboratory instrument upon which embodiments of the present teachings can be implemented.

FIG. 2 is a schematic illustration of a system used for fluorescent signal detection in accordance with implementations of the present invention. Detection system 200 is one example of a spectral detection system which can be used for RT-PCR data collection and processing in conjunction with aspects of the present invention. As illustrated, detection system 200 includes an excitation light source 202, at least one filter turret depicted by turret 204, a detector 208, a microwell tray 210 and well optics 212. Turret 204 can comprise multiple excitation filters or multiple emission filters or multiple excitation and emission filters paired for a specific dye. As illustrated, turret 204 includes filter cubes 206. A first filter cube 206A can include an excitation filter 214A, a beam splitter 216A and an emission filter 218A corresponding to one spectral species selected from a set of spectrally distinguishable species to be detected. A second filter cube 206B can include an excitation filter 214B, a beam splitter 216B and an emission filter 218B corresponding to a different spectral species selected from the set of spectrally distinguishable species to be detected.

Excitation light source 202 can be, for example, but not limited to a laser, broad spectrum light source, an LED or other type of excitation source capable of emitting a spectrum that interacts with a spectral species to be detected by system 200. In this illustrated example, light source 202 emits a broad spectrum of light filtered by either excitation filter 214A or excitation filter 214B that passes through beam splitter 216A or beam splitter 216B onto microwell tray 210 containing one or more spectral species.

Light emitted from light source 202 can be filtered through excitation filter 214A, excitation filter 214B or other filters that correspond closely to the one or more spectral species. The present teachings can be used with a plurality of spectrally distinguishable dyes such as, for example, but not limited to one or more of FAM, SYBR Green, VIC, JOE, TAMRA, NED, CY-3, Texas Red, CY-5, Mustang Purple, ROX (passive reference) or any other fluorochromes that emit a signal capable of being detected. The target spectral species for the selected excitation filter provides the largest signal response while other spectral species with lower signal strength in the band-pass region of the filter contribute less signal response. Because the multiple fluorochromes may have this overlapping excitation and emission spectra, it is useful to apply a pure-dye matrix to correct for the small amount of "cross-talk" (signal from one dye detected with more than one filter set). This process is often referred to as multicomponenting.

As presented above, the present teachings are described with reference to Real-Time Polymerase Chain Reaction (RT-PCR) instruments. In particular, an embodiment of the present teachings is implemented for RT-PCR instruments employing optical imaging of sample well plates. Such instruments can be capable of simultaneously measuring signals from a plurality of samples or spots for analytical purposes and often require calibration. An example of a process that can require calibration is the identification of ROIs or Regions of Interest.

Generally ROI calibration can be performed using a sample well plate with strong dye emissions in each cell corresponding to all filters. This can be useful since the ROIs may not be identical for each dye filter. Differences in the ROIs between filters can be caused, for example, by slight angular differences in the filters and other filter spectral characteristics. Thus, various embodiments perform per filter/per well (PFPW)-ROI calibration. These PFPW-ROI calibrations are useful to determine locations of the wells in, for example, but not limited to, a 96 well-plate, a 384 well-plate or a 3072 well array for each filter. ROI calibration can be performed using a method such as the Adaptive Mask Making teachings as described in U.S. Pat. No. 6,518,068 which is incorporated by reference herein in its entirety. The present teachings can automate the ROI calibration through minimization or elimination of user interaction. Various embodiments can automate the process by providing for software that can, for example, determine the optimal exposure time per filter using histogram analysis and a binary search pattern. The exposure time is the amount of time required to capture an image of the sample well plate. Again, this value can vary according to a filter's spectral characteristics. In general, ROI calibration can produce information defining the positions of wells in the detector's field of view. This information can be stored as mask files with either a global mask or multiple masks corresponding to different filters.

Calibration processes such as what is described above can, for example, use row and column projections and intensity profiles. This can result in ROI determinations being susceptible, for example, but not limited to artifacts and saturation inside the wells, grid rotation, variation of magnification factors and optical radial distortion. It can therefore be advantageous to have a more robust determination of ROIs to minimize such susceptibilities and remove, for example, distortions and other unwanted background noise in the detected emission data.

Background noise can refer, for example, to inherent system noise as well as other undesired signals. For example, some background noise in the data may be due to physical sources on the substrate, such as dust particles or scratches. Another example of a physical source that may provide background noise is a holder or case holding or enclosing the sample. Other background noise in the data may be due to natural radiation from the surfaces in the instrument, such as reflection and natural fluorescence. Other background noise can also be a result from the optical system detecting the emission data or the light source, for example.

The biological system may be detecting several hundred to several thousand samples, all of which may be a very small volume such as, for example, less than one nanoliter. As such, other background noise removal methods may be used alone or in combination with the calibration methods described in this document according to various embodiments to be able to determine and analyze the emission data from the sample volumes. In some embodiments, the location of samples may be more accurately determined within the substrate to perform a more accurate analysis. For example, in digital PCR analyses, being able to more accurately distinguish reactions in sample volumes versus non-reactions may produce more accurate results. Even further, according to various embodiments described herein, empty wells or through-holes may be distinguished from sample volumes in wells or through-holes that did not react, which may also be distinguished from sample volumes in wells or through-holes that did react.

According to various embodiments described herein, background noise removal may include image data analysis and processing. The method can include analyzing intensity values of the image data to interpolate the background noise that may be removed from the image of the substrate. In this way, locations of the regions-of-interest within the image may also be determined. The background noise removal may also include interpolating data from areas of the image known to include regions-of-interest. After determining the background noise over the image, the background noise may be subtracted from the image data. Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media as previously defined. Some other processes can be implemented using analog circuitry, as is well known to one of ordinary skill in the art. Additionally, memory or other storage, as well as communication components, may be employed in embodiments of the invention.

Figure 3:
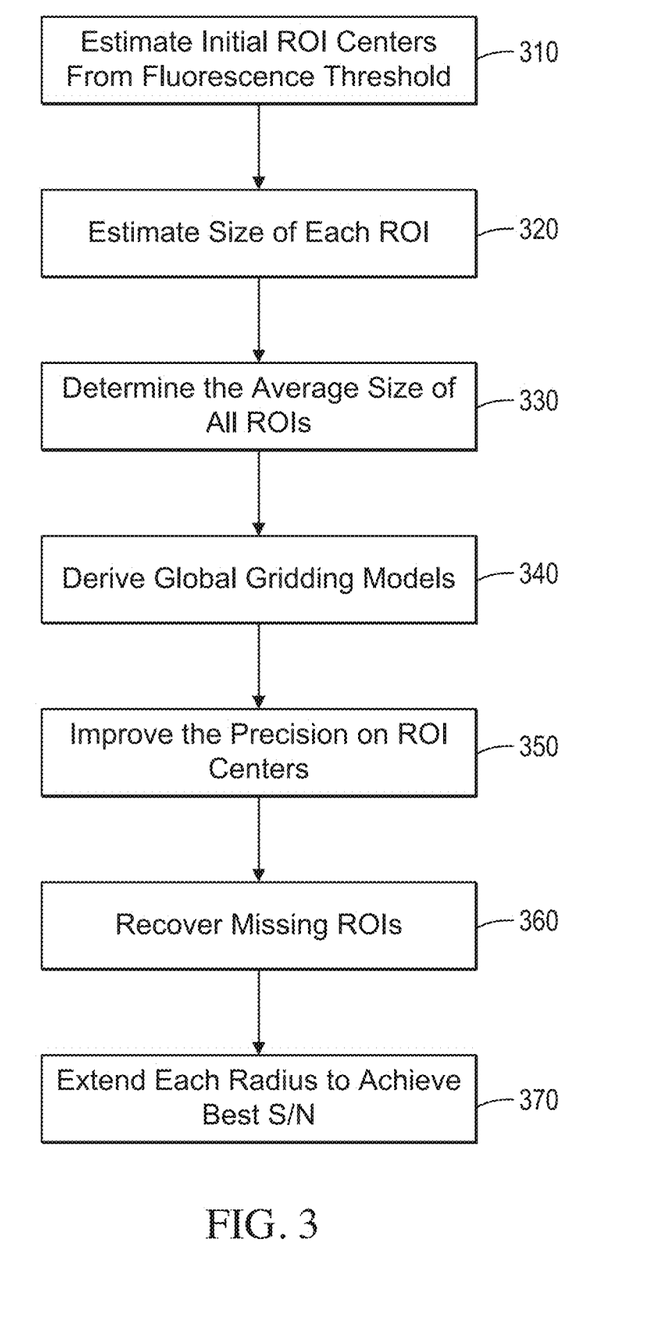
FIG. 3 illustrates a sequence of steps used in the calibration of qPCR instruments.

FIG. 3 depicts an exemplary in silico method 300 according to one embodiment of the present invention. In silico method 300 includes a plurality of set workflow subroutines in a computer readable format that can include subroutines for a biotechnology process. FIG. 3 is merely an exemplary method and the skilled artisan, in light of this disclosure, will realize that the actual number of subroutines can vary from at least about 2 subroutines to many (e.g. 2-10, 2-20, 2-30, 2-n (where n may be any number of subroutines from 3-100, 3-1000 and so on)). Each set subroutine 310-370 can include a single step or task, or optionally can include more than 1 step or task, also in a computer readable format, and each step can further include additional optional customizable steps or tasks. Each of the optional/customizable steps or tasks can have one or more optional parameters (options) that can be viewed, reviewed, set or customized by a user. In some embodiments, an in silico method of the invention includes selection by a user of at least one parameter each for each optional/customizable step of the biotechnological process using a graphical user interface (GUI) to select the at least one parameter for each optional/customizable step. In certain embodiments, every step and every parameter of the subroutines of a workflow are available to a user to view, and optionally edit. As is well known in the art, bioinformatics programs typically hide some of these parameters and/or steps from users, which causes user frustration and inefficiency especially when the result of an in silico designed experiment is not the expected result for a user.

An exemplary in silico method of the disclosure illustrated generally in FIG. 3 can be carried out, performed or executed by generating at least one method file in a computer system, the method file comprising computer readable instructions for a plurality of subroutines (10, 20, 30 . . . ) of customizable steps (A, B, C) each of which may have one or more parameters that may be, for example, viewed, selected, changed or inputted; and performing the biotechnological process in silico comprising executing the at least one method file comprising computer readable instructions by the computer system to obtain at least one biotechnology product.

In some embodiments, at least one customizable/optional parameter is selected from a default parameter, wherein the default parameter is stored in a component of the computer system (such as storage, database etc.).

Referring again to FIG. 3, the first step in calculating ROI locations is to estimate the initial ROI centers from the fluorescence thresholds in step 310. A sample plate configured to contain a plurality of biological samples is provided and inserted into an analytical instrument capable of analyzing biological samples through the process of PCR. Each biological sample is contained in a sample well and can be excited by a light source and in response to the excitation can fluoresce at a predetermined wavelength which can be detected by a fluorescence detector. As presented above with regards to FIG. 2, light source 202 can be a laser, LED or other type of excitation source capable of emitting a spectrum that interacts with spectral species to be detected by system 200. Additionally, biological samples can include spectrally distinguishable dyes such as one or more of FAM, SYBR Green, VIC, JOE, TAMRA, NED, CY-3, Texas Red, CY-5, ROX (passive reference) or any other fluorochromes that emit a signal capable of being detected.

Prior to exciting the biological samples, input parameters and algorithm parameters are set to provide an estimated starting point for the ROI determination. Input parameters can include, for example, but not limited to threshold range and step, well size, well center-to-center distance, spacing between sub-arrays, optical pixels per millimeter and plate layout. The plate layout can include the total number of wells and the configuration of the sample wells. A frequently used configuration can be a rectangular array comprising a plurality of rows and a plurality of columns however, one skilled in the art will understand that the configuration can be any geometry suitable for the instrument being used. Further, the total number of wells can vary. One skilled in the art will be familiar with configurations totaling from 1 well to thousands of wells in a single sample plate or sample containment structure. The ROI finding algorithm parameters can set acceptable ranges for well size, well center-to-center distance and minimum circularity. Circularity is a calculated value and can be, for example, a ratio of the perimeter to the area.

Once the input parameters and the algorithm parameters have been determined, the plurality of samples can be excited with energy from an appropriate light source, and images can be collected of the fluorescence emitted from each sample well in the sample plate. The fluorescence images of the sample plate can be further analyzed to select ROI candidates based on the input parameters and the algorithm parameters. The ROI candidates that satisfy the parameters can be saved for further analysis and the size and circularity of each well are determined in step 320. ROI candidates that do not satisfy the parameters can be discarded along with any locations that did not fluoresce. The retained ROI candidates can be further evaluated to determine the distance between ROIs based on the well-to-well spacing parameter and the allowed range parameter for the well-to-well spacing. ROIs that have centers that are in close proximity to each other based on the well-to-well parameters can be considered to be the same sample well, and the one with the best circularity is selected as the ROI for that well. Once all the ROI candidates have been determined, the average well size can be calculated, the average can be assigned to each sample well ROI in step 330 and the initial estimated ROIs can be saved.

The expected well locations can be arranged in a grid pattern. The grid pattern can be determined based on the plate layout parameter. This parameter can include the number of wells, number of columns and number of rows in the whole plate or sub-array where each well has an expected set of XY grid co-ordinates based on the plate layout parameter. Further analysis can now be initiated on the initial estimated ROIs to better define the locations of each initial ROI and can be referred to as global gridding. The first step in global gridding is to analyze the centers of the initial estimated ROIs to find adjacent ROIs. This can be determined by comparing the center-to-center distance between ROIs to the grid co-ordinates based on the plate layout. The XY grid co-ordinates can then be determined for each of the initial estimated ROIs based on the spatial relationship between ROIs.

In order to improve the precision of the ROI locations it can be advantageous to relate the center-to-center ROI co-ordinates to the grid co-ordinates of the plate layout. This can be accomplished by determining and applying mapping functions. Mapping functions are a pair of 2-dimensional quadratic polynomial functions. These functions are calculated to map X (or Y) grid locations to the ROI center locations in the X (or Y) direction. Once the mapping functions have been determined, they can be applied to the expected grid co-ordinates to provide several benefits. First the precision of the ROI center locations can be improved, second it can be possible to recover ROIs that were missing during the initial ROI finding, the well-to-well center distance in the images can be calculated which can be used to determine the actual well size in the images.

Further adjustment of ROIs can provide additional benefits to optical performance. The inventors discovered that there was a relationship between ROI size and the signal-to-noise ratio (SNR) of the optical system. One skilled in the art would know that there are several mathematical functions to calculate SNR of electrical and optical systems. The inventors characterized SNR with Equation 1 below:

$$SNR = \frac{S_{dye\ plate} - S_{dye}}{\sqrt{\frac{S_{dye} + S_{SG} - 2N \times offset}{G} + 2N\sigma_{R,y}^2}}$$

where: SNR=Signal to Noise Ratio
$S_{dye\ plate} = S_{dye}$
$S_{BG}$=the sum of all pixel intensities within ROIs from background images
$S_{dye}$=the sum of all pixel intensities within ROIs from the dye images
N=the number of pixels within an ROI
offset=the camera offset
G=the camera gain
$\delta^2_{R,y}$=the read noise An experiment was conducted using an optical system that included six pairs of filters. Each pair of filters included an excitation filter (Xn) and an emission filter (Mn). Each filter was sensitive to a narrow band of wavelengths that corresponded to the excitation frequency and emission frequency corresponding to a fluorescent dye configured to be compatible with the PCR process. In addition, ROIs were optimized according to the teachings presented in this document. In order to study the effect of ROI size on signal-to-noise, fluorescence was detected from a 96 well sample plate using 6 pairs of filters. The radius of each ROI was extended incrementally by 1 pixel. Equation 1 was used to calculate the SNR for each of 6 filter pairs and each pixel increment. The results of the experiment are shown below in Table 1:

TABLE 1

| SNR | X1M1 | X2M2 | X3M3 | X4M4 | X5M5 | X6M6 |
|---|---|---|---|---|---|---|
| ΔR = 0 | 1709.5 | 2502.7 | 1840.3 | 1613.8 | 1632.4 | 475.5 |
| ΔR = 1 | 1808.2 | 2642.0 | 1942.7 | 1706.3 | 1709.2 | 496.8 |
| ΔR = 2 | 1826.6 | 2677.8 | 1964.2 | 1722.7 | 1718.8 | 491.2 |
| ΔR = 3 | 1818.7 | 2678.7 | 1958.4 | 1714.4 | 1708.2 | 479.0 |
| ΔR = 4 | 1802.5 | 2667.3 | 1943.1 | 1697.6 | 1690.8 | 464.7 |

The bold entries identify the highest SNR for each of the 6 filter pairs, and a 2 pixel radius extension (ΔR=2) provides an overall improvement in SNR of approximately 6% across the 6 filter pairs.

Figure 4:
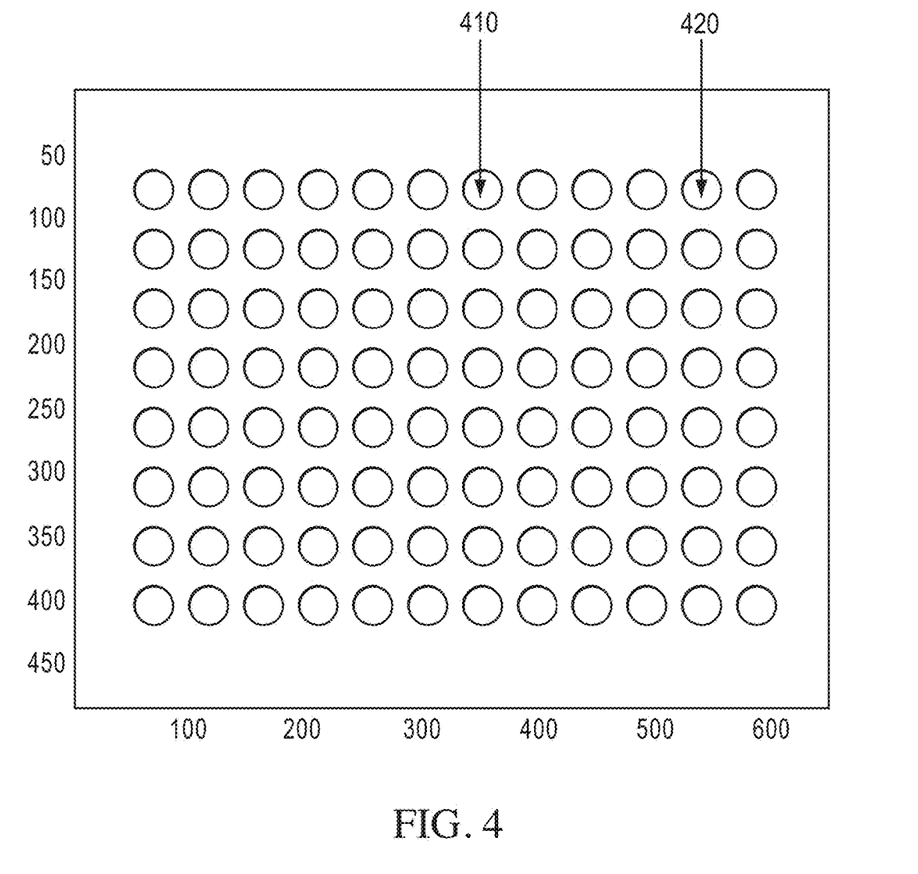
FIG. 4 illustrates the regions-of-interest for a 96 well sample container.

FIG. 4 shows an image of a sample plate with 96 wells 410. Each of the 96 wells 410 produced a fluorescent image. After applying the teachings of this document ROIs were optimized and the blue circles identify the ROI for each well position. To test the robustness of the teachings, several test cases were conducted.

Figure 5:
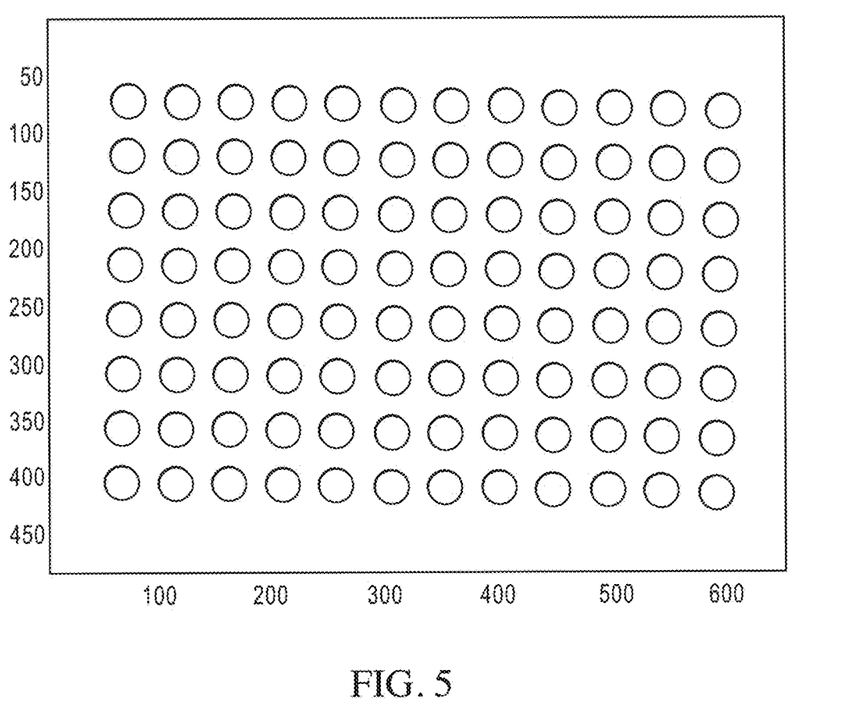
FIG. 5 illustrates the regions-of-interest for a rotated 96 well sample container.

Test case 1 is shown in FIG. 5. An ROI channel image was manually rotated by 1° counter-clockwise and the ROI teachings were applied to the image. The result in FIG. 5 shows that the ROI algorithm located all 96 ROIs in spite of the rotation.

Figure 6:
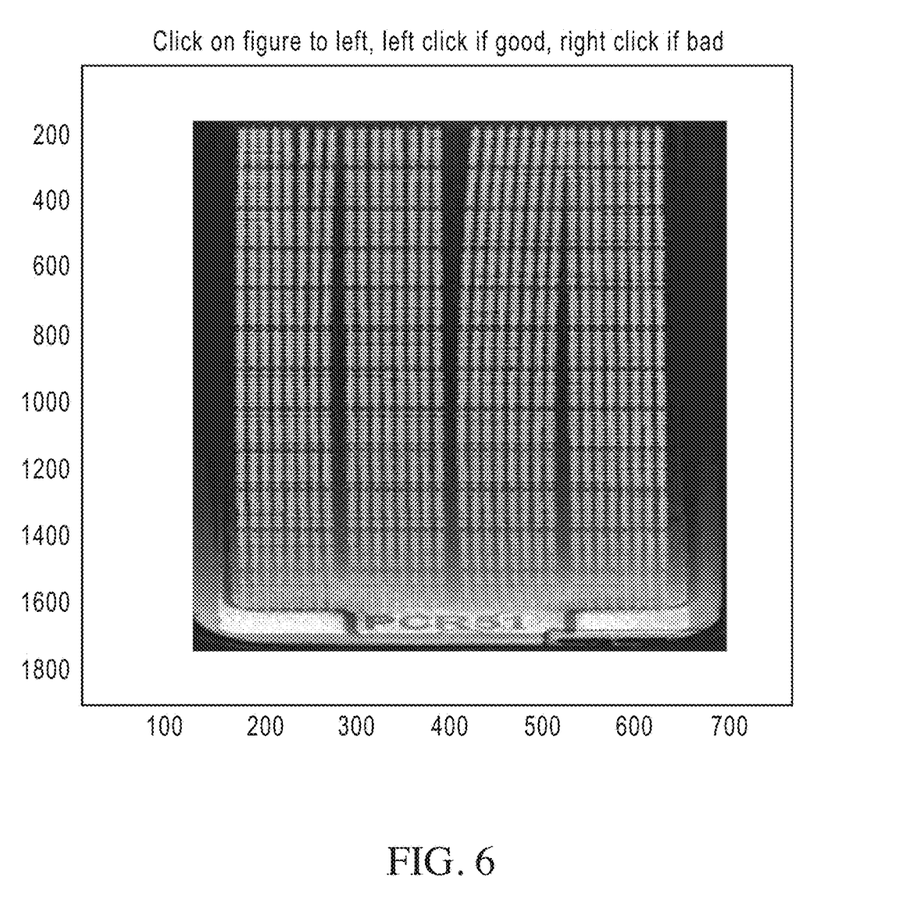
FIG. 6 illustrates a sample array with incorrectly located regions-of-interest.
Figure 7:
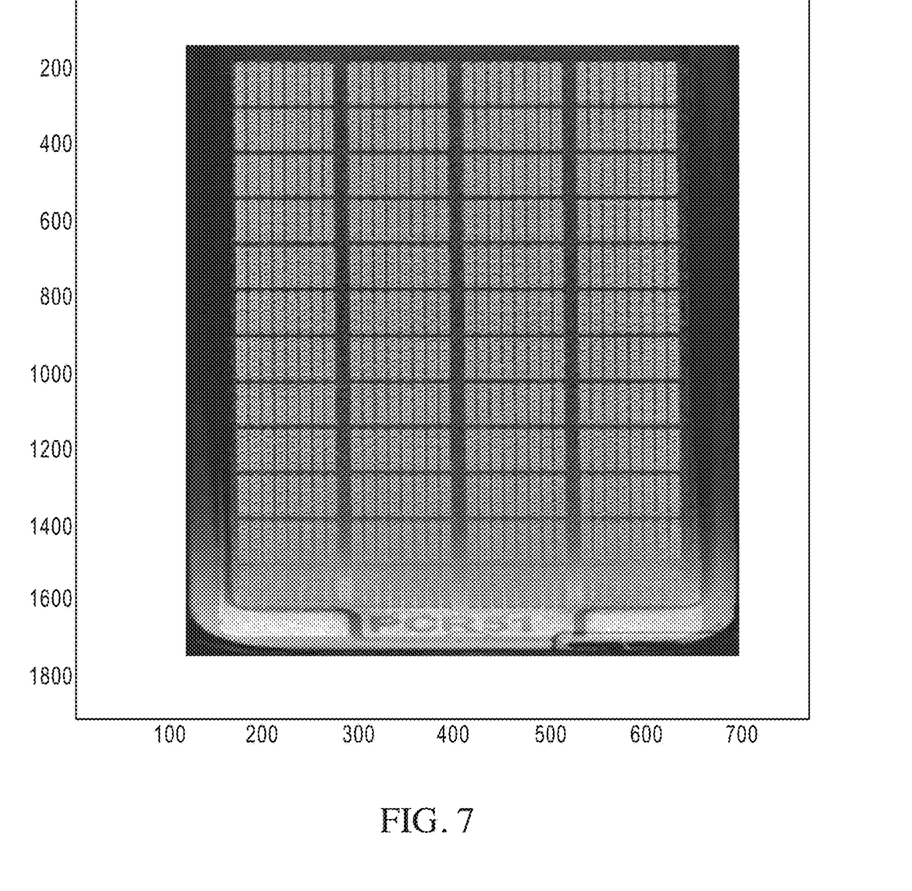
FIG. 7 illustrates a sample array with correctly located regions-of-interest.
Figure 8:
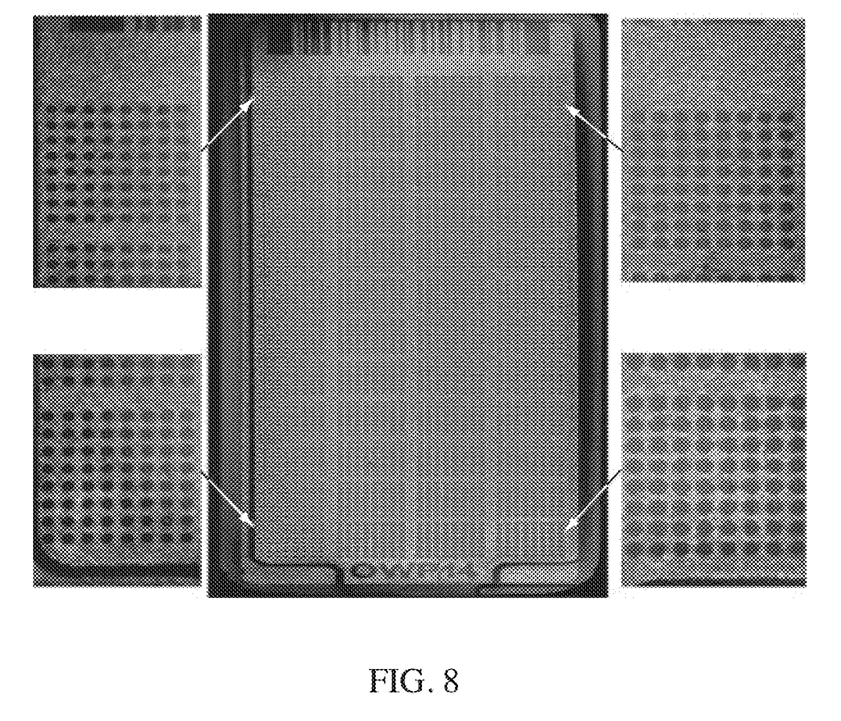
FIG. 8 illustrates a closer view of a sample array with correctly located regions-of-interest.

Test case 2 is shown in FIG. 6 and depicts a failure in determining ROIs for an array having 3072 well locations due to illumination non-uniformity and optical distortion. The failure in the alignment of the ROIs can be seen at the top of the image as bending to the right of the columns of the ROIs. The same image was submitted to the algorithm taught in this document and the results are presented in FIG. 7. It can clearly be seen that the teachings of the present invention corrected the distortion previously shown in FIG. 6. The precision of ROI locations is also depicted in FIG. 8.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a monomer" includes two or more monomers.

It will be apparent to those skilled in the art that various modifications, variations and optimizations can be made to various embodiments described herein without departing from the spirit or scope of the present teachings. Thus, it is intended that the various embodiments described herein cover other modifications, variations and optimizations within the scope of the appended claims and their equivalents.

What is claimed:

1. A method for the calibration of a laboratory instrument comprising:
   providing an optical system comprising a light source capable of imaging fluorescence emission from a plurality of biological samples upon excitation by the light source, where each biological sample is contained in one of a plurality of sample wells on a sample well plate;

estimating at least one initial region of interest (ROI) by using the optical system to detect fluorescence emissions at the plurality of sample wells in relation to one or more fluorescence thresholds from each sample well;
estimating one or more center locations of each ROI;
estimating a size of each ROI;
determining an average size of the ROIs from the plurality of sample wells;
deriving one or more global gridding models, wherein the global gridding models analyze the estimated center locations of each ROI;
applying the global gridding models to improve the precision of the ROI center locations by relating the estimated center locations to one or more location coordinates of a layout of the sample well plate;
recovering missing ROIs with one or more mapping functions of the global gridding models; and
adjusting the sizes of the ROIs, wherein the adjustment improves the signal-to-noise ratio of the optical system.

2. The method of claim 1, wherein each biological sample comprises one or more spectrally distinguishable dyes.

3. The method of claim 2, wherein the one or more spectrally distinguishable dyes comprises at least one of FAM, SYBR Green, VIC, JOE, TAMRA, NED, CY-3, Texas Red, CY-5, Mustang Purple, or ROX.

4. The method of claim 1 wherein the biological sample fluoresces at a predetermined wavelength in response to the excitation.

5. The method of claim 1 wherein the laboratory instrument is configured to analyze the one or more biological samples through the polymerase chain reaction (PCR) process.

6. The method of claim 1 wherein the light source comprises a laser, light emitting diode (LED), or broad spectrum light source.

7. The method of claim 1 wherein the global gridding models comprise comparing the center-to-center distance between ROIs to grid co-ordinates of a well plate layout to determine an X and Y grid co-ordinate for each ROI.

8. The method of claim 7 further comprising determining and applying mapping functions to map each grid co-ordinate to an ROI center.

9. A system for calibrating region of interest (ROI) locations for one or more biological samples in a laboratory instrument, the system comprising:
an optical detection system comprising:
a plurality of filters;
at least one excitation source;
at least one detector configured to collect one or more images of fluorescence emissions from the one or more biological samples upon excitation by the at least one excitation source; and
a microwell tray comprising a plurality of sample wells where each biological sample is contained in a sample well; and
a computer system comprising:
at least one processor configured to:
set estimates of one or more ROI center locations based on the one or more images of fluorescence emissions from the one or more biological samples, and one or more input parameters received from a user;
estimate a size of each ROI;
determine an average size of the ROI from a plurality of sample wells;
analyze the estimated ROI center locations to find adjacent ROIs;
improve the precision of the ROI center locations by applying one or more mapping functions to relate the estimated center locations to one or more location coordinates of a layout of the microwell tray;
recover missing ROIs with the one or more mapping functions; and
adjust the sizes of the ROIs, wherein the adjustment improves the signal-to-noise ratio of the optical detection system;
at least one computer-readable medium;
at least one input device coupled to the at least one processor and configured to receive the one or more input parameters from the user; and
at least one display.

10. The system of claim 9 wherein the at least one computer-readable medium is coupled to the processor.

11. The system of claim 10 wherein the computer-readable medium comprises instructions executable by the processor.

12. The system of claim 11 wherein the instructions executed by the processor comprise at least one step for determining ROIs and automating the calibration of the ROI locations.

13. The system of claim 9 wherein the plurality of filters comprises at least one excitation filter, at least one emission filter and at least one beam splitter.

14. The system of claim 9 wherein the at least one biological sample comprises at least one fluorescent dye.

15. The system of claim 9 further comprising a graphical user interface (GUI) configured to enable a user to select the one or more input parameters.

16. The system of claim 9 wherein the one or more input parameters include one or more of: threshold range and step, well size, well center-to-center distance, spacing between sub-arrays, optical pixels per millimeter and plate layout.

17. The system of claim 9 wherein the at least one input device comprises alphanumeric and other keys configured to communicate information to the processor.

18. The system of claim 17 wherein the at least one input device further comprises cursor control to communicate direction information to the processor.

19. The system of claim 9 wherein the plurality of sample wells are arranged in a grid pattern comprising one or more plate layout parameters.

20. The system of claim 19 wherein the one or more plate layout parameters comprise a number of wells, a number of columns, and a number of rows, wherein each well comprises a set of XY coordinates.

* * * * *